(12) United States Patent
Akerfeldt et al.

(10) Patent No.: US 6,860,895 B1
(45) Date of Patent: Mar. 1, 2005

(54) TOOL, A SEALING DEVICE, A SYSTEM AND A METHOD FOR CLOSING A WOUND

(75) Inventors: Dan Akerfeldt, Uppsala (SE); Per Egnelov, Uppsala (SE); Fredrik Preinitz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/018,137

(22) PCT Filed: Jun. 18, 1999

(86) PCT No.: PCT/SE99/01114
§ 371 (c)(1),
(2), (4) Date: Mar. 20, 2002

(87) PCT Pub. No.: WO00/78226

PCT Pub. Date: Dec. 28, 2000

(51) Int. Cl.$^7$ .............................. A61D 1/00; A61B 17/08
(52) U.S. Cl. ...................... 606/215; 606/139; 606/151; 606/213; 606/216; 606/217
(58) Field of Search ................................ 606/116, 117, 606/139, 142, 151, 213, 215–217; 292/314

(56) References Cited

U.S. PATENT DOCUMENTS

| | | | | |
|---|---|---|---|---|
| 3,760,627 A | * | 9/1973 | Richardson et al. ... | 29/243.523 |
| 4,796,612 A | * | 1/1989 | Reese .......................... | 606/72 |
| 5,098,433 A | * | 3/1992 | Freedland ................... | 606/63 |
| 5,116,349 A | * | 5/1992 | Aranyi ..................... | 227/181.1 |
| 5,250,049 A | * | 10/1993 | Michael ...................... | 606/72 |
| 5,342,393 A | * | 8/1994 | Stack ......................... | 606/213 |
| 5,350,399 A | | 9/1994 | Erlebacher et al. ......... | 606/213 |
| 5,433,053 A | * | 7/1995 | Tulloch ...................... | 52/582.1 |
| 5,531,759 A | | 7/1996 | Kensey et al. .............. | 606/213 |
| 5,593,422 A | * | 1/1997 | Muijs Van de Moer et al. | 606/213 |
| 5,666,710 A | * | 9/1997 | Weber et al. .......... | 29/243.523 |
| 5,800,436 A | * | 9/1998 | Lerch .......................... | 606/72 |
| 5,861,003 A | * | 1/1999 | Latson et al. ............... | 606/213 |
| 5,928,264 A | * | 7/1999 | Sugarbaker et al. ........ | 606/207 |
| 6,024,756 A | * | 2/2000 | Huebsch et al. ............ | 606/213 |
| 6,045,551 A | * | 4/2000 | Bonutti ....................... | 606/60 |
| 6,074,401 A | * | 6/2000 | Gardiner et al. ............ | 606/139 |
| 6,270,500 B1 | * | 8/2001 | Lerch .......................... | 606/72 |
| 6,379,363 B1 | * | 4/2002 | Herrington et al. .......... | 606/79 |
| 6,425,911 B1 | * | 7/2002 | Akerfeldt et al. ........... | 606/213 |
| 6,491,714 B1 | * | 12/2002 | Bennett ...................... | 606/232 |
| 6,508,828 B1 | * | 1/2003 | Akerfeldt et al. ........... | 606/215 |

* cited by examiner

Primary Examiner—Julian W. Woo
Assistant Examiner—Michael Mendoza
(74) Attorney, Agent, or Firm—Foley & Lardner LLP

(57) ABSTRACT

A tool (101) is provided for inserting and mating two plug members (2, 3) of a sealing device (1) for closing a wound in the wall of a vessel by placing the distal plug member (2) of the sealing device inside the vessel and the proximal member (3) on the outside of the vessel. The distal plug member is provided with an elongated retracting means (6) extending from the distal plug member. The tool comprises a gear mechanism (32) coupled to the retracting means for converting a movement of the tool in a proximal direction away from the wound (22), when the distal plug member is anchored in the vessel (20), to a pushing movement for moving the proximal plug member in a direction towards the distal plug member in response to a stretching force in the retracting means.

22 Claims, 7 Drawing Sheets

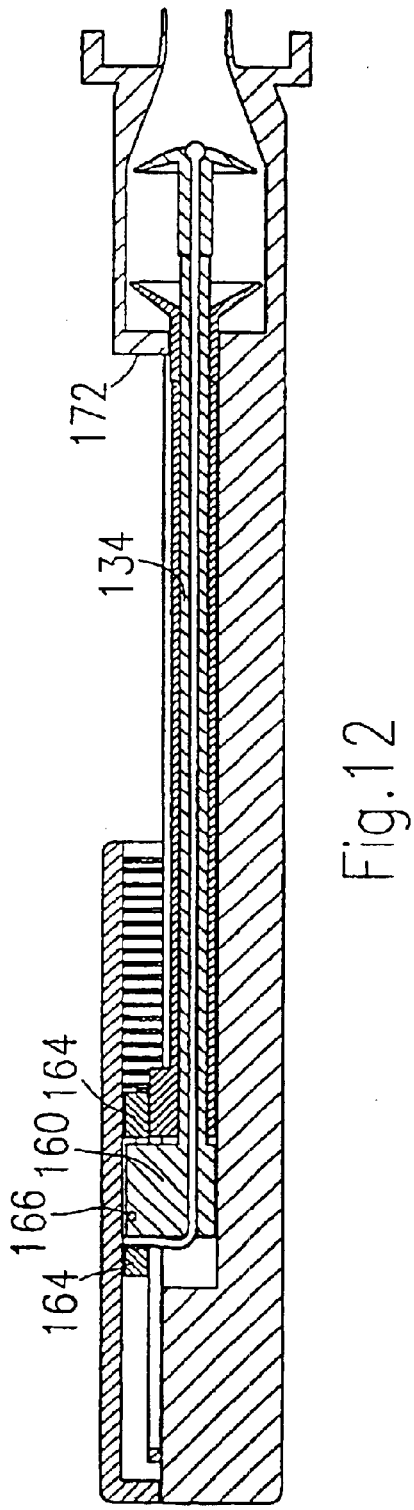
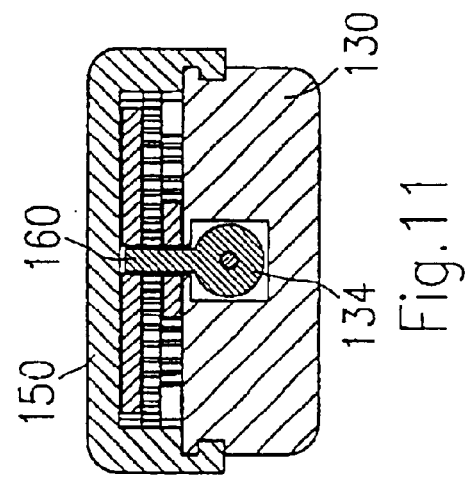
Fig. 12
Fig. 11

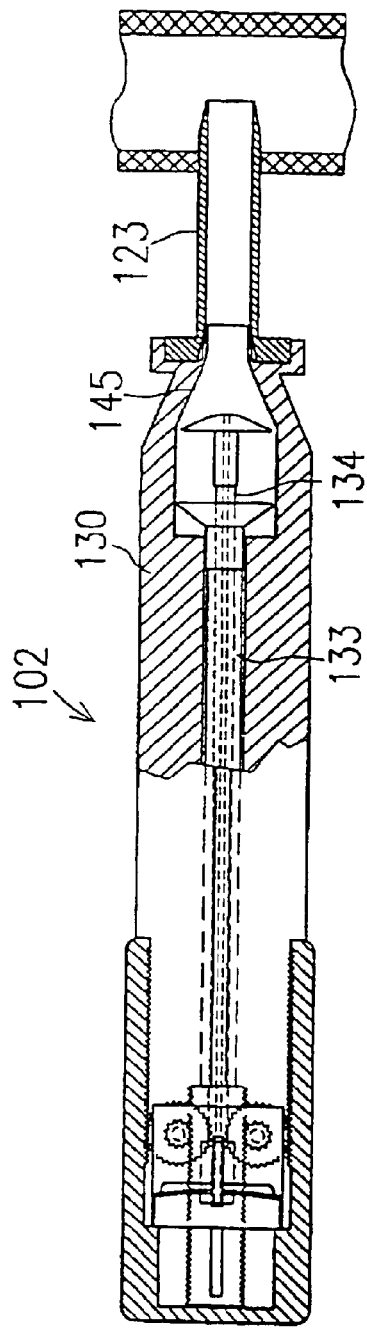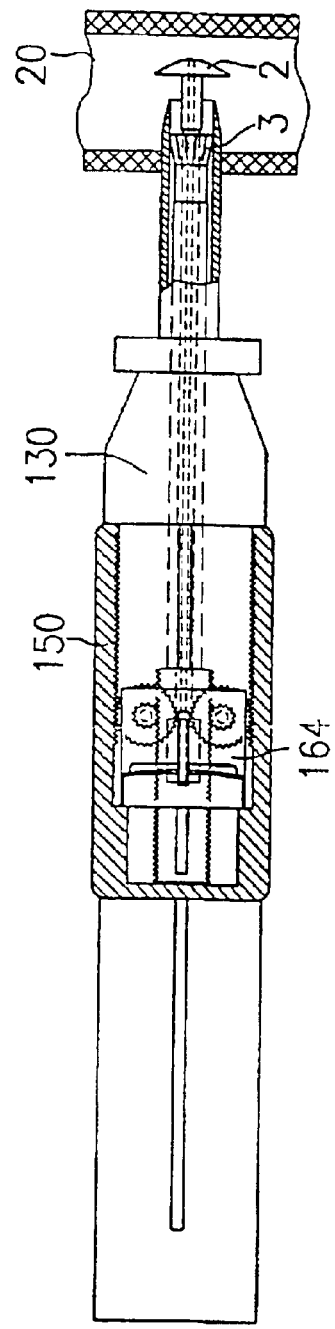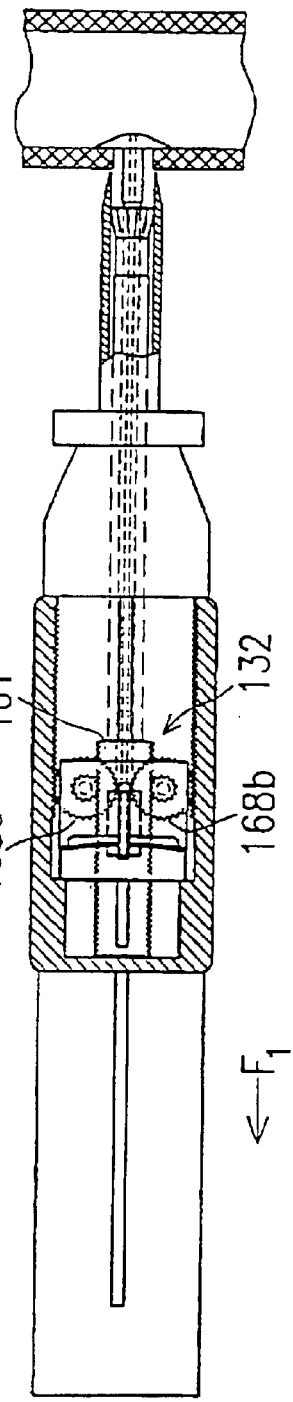

US 6,860,895 B1

TOOL, A SEALING DEVICE, A SYSTEM AND A METHOD FOR CLOSING A WOUND

SCOPE OF THE INVENTION

The present invention relates to medical devices, and more specifically to a system for introducing a flexible two-piece wound closure plug in a punctured vessel of a human or animal body.

PRIOR ART

A sealing device for sealing an arterial puncture is described in U.S. Pat. No. 5,350,399 to Erlebacher et al. A first closure member, that is resiliently expandable into a circular disc shape, is positioned within a punctured vessel. A second closure member, also being resiliently expandable into a circular disc shape, is movably fitted onto a guide means being integrally formed with the first closure member. The guide means has a saw tooth shape to hold the second closure member. The guide means also acts as a retracting means, i.e. a means for holding the first closure means towards the wound edge, when the first and second closure members are mated.

A tool for mating said first and second closure members is also disclosed in U.S. Pat. No. 5,350,399. Initially, the first closure member and its integrated guide means is pushed into the artery through a percutaneous sheath, normally used for a treatment preceding the closure of the wound. Thus, the tool is not used for insertion of said first member. Then, the guide means of the first closure member is passed through the tool, wherein the second closure member is stored in a folded state. Then, the second closure member is pushed out of the tool to be fitted onto the guide means of the first member by operating a trigger of the tool. The force with which the second closure member is mated to the first closure member is visually represented by a force/pressure gauge to avoid to much pressure onto edge of the wound. The tool is also used to cut the guide means when the mating is completed.

A similar closure means is disclosed in U.S. Pat. No. 5,342,393 to Stack.

In U.S. Pat. No. 5,531,759 to Kensey et al is described a tool for sealing a percutaneous puncture wound in a vessel with a sealing device, the sealing device including a substantially rigid anchor member for insertion into the vessel and a sealing member to be pressed to the outside of the vessel.

TECHNICAL BACKGROUND

A puncture wound in a blood vessel typically results from a surgical treatment, such as treatment of a vascular disease, such as atherosclerosis.

It is known to close such a wound with a two-piece plug device having a distal member that is inserted in the vessel and a proximal member that is tightened towards the distal member with the vessel wall, i.e. the edge of the wound, clamped between the plug members.

Such plugs are described in U.S. Pat. Nos. 5,350,399 and 5,342,393, respectively. In both these inventions, however, the retracting means used to transfer a holding force to the intra-arterial closure member is integrally formed with the intra-arterial closure member and is therefore formed of the same material. This limits the possibilities to manipulate the intra-arterial closure member with a tool.

Furthermore, tools presently known are complicated to handle in that they require numerous different grips to perform the closing of the wound.

They also require the complete attention from the operator in order to avoid misplacement of the closure members. A misplaced closure plug is difficult to remove, and could even call for surgery.

Furthermore, it is essential not to stress the wound too hard in order to avoid rupture of the wound edge. At the same time it is essential to apply a sufficient mating force to the closure members to obtain a leakage-free closing of the wound.

Therefore, there is a need for a method and a system that offers a simple and safe closing of a punctured vessel.

SUMMARY OF THE INVENTION

In a first aspect, it is an object of the present invention to provide a tool for a simple and safe securing of a two-piece wound closing plug around the edge of a puncture wound in a vessel in a human or animal body, thereby obstructing blood leakage through the wound.

This object is achieved with the tool device according to claim 1.

The plug is divided into two plug members prior to insertion in the wound. The tool according to the invention includes a compartment for holding the plug members in a folded shape, means for pushing the plug members out of the plug compartment and a gear mechanism for converting a movement of the tool in a direction from the wound to a movement of the plug pushing means to mate and compress the plug members to form a substantially leakage free wound closure plug.

In a second aspect, it is an object of the present invention to provide a plug for use with the tool according to the invention.

This object is achieved with the sealing device according to claim 7.

The plug according to the invention consists of a distal and a proximal plug member. A central bore through the proximal plug member fits on a cylindrical post centrally protruding from the proximal surface of the distal plug member. The surfaces of the central bore and the cylindrical post, respectively, are provided with projections and corresponding recesses to provide a one-way snap fitting. A central through hole is provided in the cylindrical post of the distal plug member to accommodate a flexible retracting means, such as a biodegradable suture.

Since the retracting means is separate from the distal plug member the distal plug member has an improved flexibility within the artery to adapt to the inner artery wall. At the same time, simplified manufacturing of the distal plug member is obtained.

In a third aspect of the present invention, it is an object to provide a simple and safe method for closing a puncture wound in a vessel.

This object is achieved with the method according to claim 9.

According to the method of the invention, a two-piece plug is inserted into the wound with a specially designed tool. A lever is pushed against the wound to push out the distal plug member of the two-piece plug into the vessel. Then, by simply drawing the tool away from the wound the proximal plug member is pushed out of the tool, the plug members are compressed to form a closure plug that encloses the wound edge in a safe grip and finally the tool is completely removed from the wound to leave only a retracting means (such as a suture) attached to the closure plug. The retracting means is easily cut to a desired length.

BRIEF DESCRIPTION OF ATTACHED DRAWINGS

The present invention shall now be described by way of example and with reference to the attached drawings, wherein:

FIG. 11 is a cross sectional view of the tool according to FIG. 8, seen along the line BB in FIG. 8.

FIG. 12 is a cross sectional view of the tool according to FIG. 8, seen along the line C—C in FIG. 8.

FIG. 13 is a cross sectional view of the second embodiment of the tool of the invention, in a state prior to closing a wound.

FIG. 14 is a cross sectional view of the embodiment of FIG. 13, when inserting the distal member of a closure plug.

FIG. 15 is a cross sectional view of the embodiment of FIG. 13, when retracting the introducer from the wound.

DETAILED DESCRIPTION OF PREFERRED EMBODIMENTS

First, a plug being preferred for use with the invention shall be described with reference to FIGS. 1 and 2.

Figure 1:
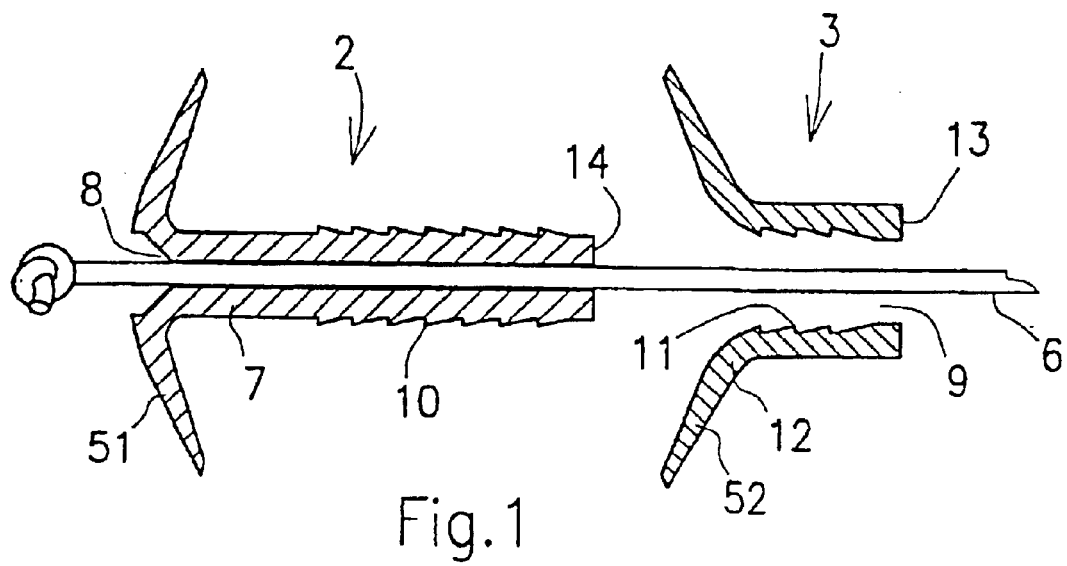
FIG. 1 is a cross sectional view of an embodiment of the components of a plug device for use with the tool of the invention.
Figure 2:
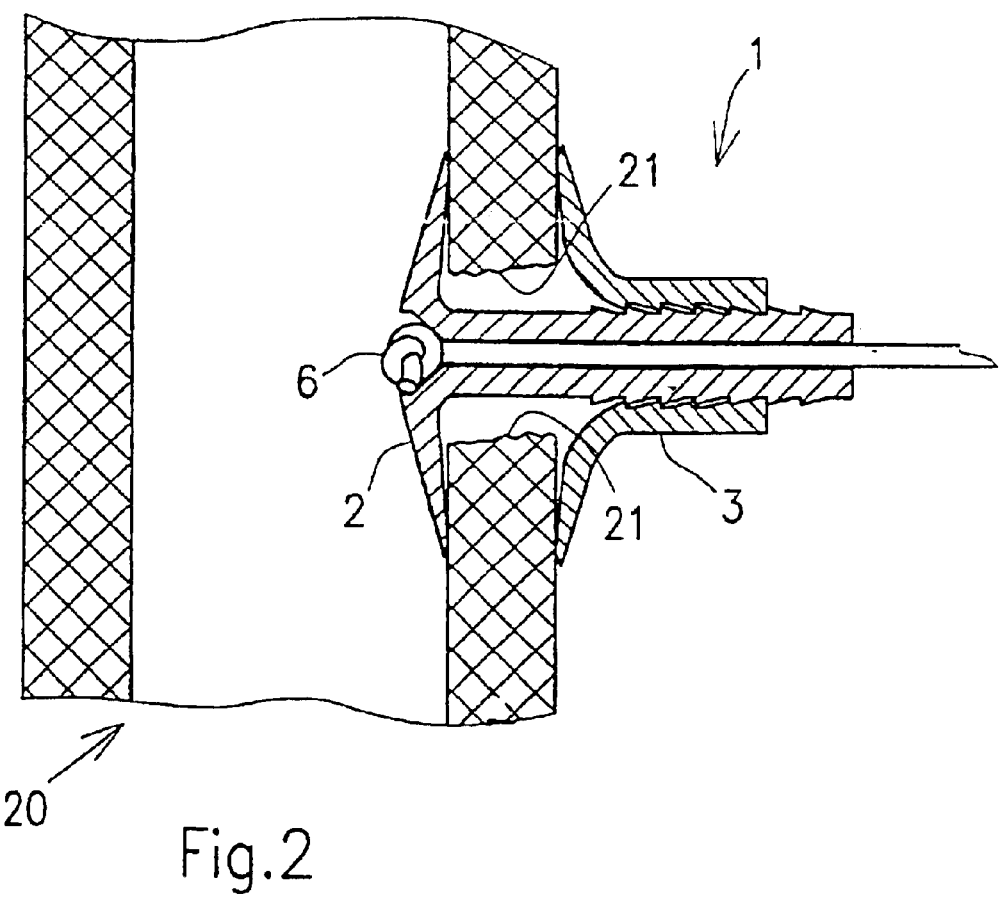
FIG. 2 is a cross sectional view of the components of FIG. 1 assembled to form a wound closure plug according to the invention.

The plug 1 according to FIGS. 1 and 2 includes two generally circular main members: a distal plug member 2 and a proximal plug member 3 being made of a flexible biodegradable material, such as lactide/glycolide polymer or polydiaxonone. A foldable generally umbrella-shaped disc portion 51 is formed at the distal end of the distal plug member 2, and a similarly generally umbrella-shaped disc portion 52 is formed at the distal end of the proximal plug member 3. The umbrella-shaped disc portion are formed such that their edges are directed toward each other when then plug members are assembled to form a plug.

The distal plug member 2 is designed to be inserted inside a punctured vessel 20, while the proximal plug member 3 is designed to be provided at the outside of the vessel 20.

The distal plug member 2 is provided with a substantially cylindrical central post 7 protruding in a direction out from the vessel, i.e. in the proximal direction, when 29 the plug member 2 is inserted in the vessel. A central bore 8 extends axially through the post 7.

The proximal plug member 3 is provided with a central sleeve section 12 protruding in a direction away from the wound when the plug member 3 is positioned on the outside of the vessel. A central bore 9 extends axially through the sleeve section 12 and is designed to receive the post 7 of the distal plug member 2 when the members are clamped together, as will be described below.

When pressed together, the plug members 2, 3 clamp the edge 21 of the wound in the vessel between the edges of their umbrella-shaped portions 51, 52.

The central bore 9 of the proximal plug member 3 is adapted to be snap fitted onto the post 7 of the distal plug member 2. For that purpose, the bore 9 and the post 7, respectively, are provided with corresponding saw tooth profiles 10, 11. The saw tooth profiles 10, 11 are so arranged that the proximal plug member 3 can be pressed onto the post 7 of the distal plug member 2 with a force. Thereafter, the plug members can only be separated using a considerable force.

Therefore, no separate retaining means is necessary for holding the plug members securely connected.

The post 7 of the distal plug member 2 has a proximally directed end surface 14. Similarly, the sleeve 12 of the proximal plug member 3 has a proximally directed end surface 13.

A string shaped retracting means 6, preferably a suture, is thread through the bore 8. The end of the suture 6 is prevented from passing through the bore when a tension force is applied to it with an enlarged portion. The enlarged portion could, for example, be formed by attaching a small amount of a plastic material, but the simple way of providing a knot, as shown in FIGS. 1 and 2, is preferred.

In order to avoid that the suture will slip out of the bore and into the vessel, subsequent to the closing of the wound as will be explained later, it should also be fixed to the bore. This could be achieved by clamping means arranged in or near the bore, but it is preferred to attach the suture in the bore 8 with a small amount of an adhesive (not shown). Although adhesive alone could be used for securing the suture to the bore, the use of the knot is preferred for safety reasons.

It should be noted that although the closure plug and the retracting means described above are suited for use with the tool of the invention, as will be described in the following, they could be used for closing a puncture wound in a vessel also when any other suitable insertion tool is used.

A first embodiment of an inserting tool 101 according to the invention shall now be described with reference to FIGS. 3-7. It should be noted that in order to make the figures easy to read, a complete set of referral numbers are not provided in each figure.

It is preferred to use the tool to insert a closure plug as disclosed above, but it should be noted that any plug design suitable to cooperate with the inserting tool could be inserted with the tool of the invention. The reason for preferring the plug according to the present invention is that the use of a separate retracting means, such as a suture, as will be described below provides an improved flexibility of the distal plug member 2 to adapt to the inner wall of the vessel. The use of a suture is also advantageous for performing the wiring in the gear mechanism, as will be described below.

Furthermore, the use of generally umbrella-shaped plug members is advantageous in that an even pressure is applied to the wound edge, thereby reducing the risk for wound edge rupture. The disk shape of the plug members also provides improved possibility to achieve a non-leaking closure. However, the present invention is adaptable for use with other types of plug members, such as those described in U.S. Pat. No. 5,531,759.

Figure 3:
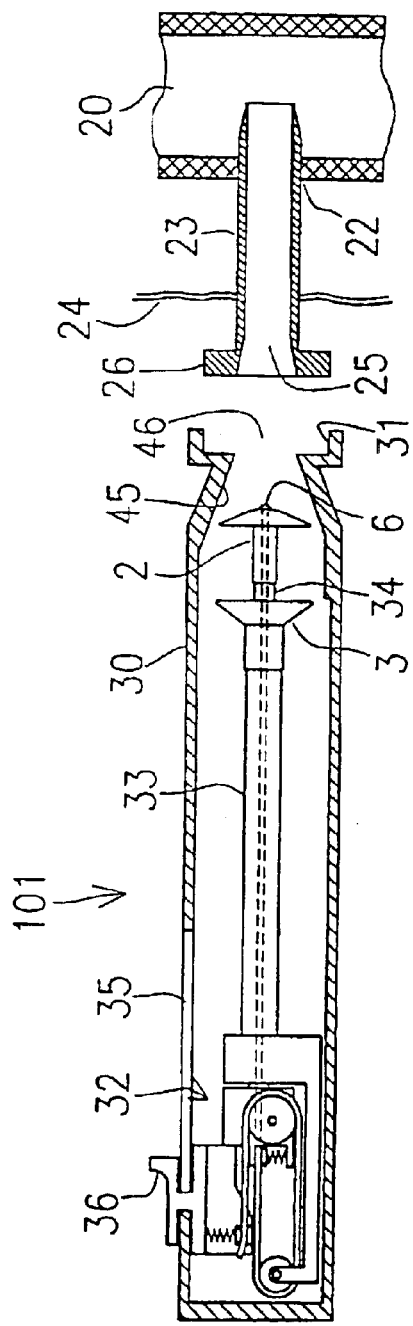
FIG. 3 is a cross sectional view of a first embodiment of the tool of the invention, in a state prior to closing a wound.

The inserting tool should be used with an introducer 23. Any introducer being well known in the field of surgical treatment through a blood vessel could be used provided that a fitting 31 of the inserting tool 101 is adapted to a corresponding fitting 26 of the introducer 23 (or is coupled with any suitable separate means, such as clamps). Also, the dimensions of the inserting tool components should be adapted to the introducer, as will be understood from the following description. In FIG. 3 the skin of the patient is indicated with the referral number 24.

As is shown in FIG. 3, the inserting tool comprises an elongated casing 30 enclosing a gear mechanism or movement direction reverser 32, an outer feeding means or outer feed boom 33, an inner feeding means or inner feed boom 34, a proximal plug member 3, a distal plug member 2 and a suture 6 (forming a retracting means). The wiring of the suture 6 through the plug members 2, 3 is clearly shown in FIG. 1 and FIG. 2.

An elongated opening extends through the casing 30 in the axial direction. An insertion lever or pusher 36 extends through the opening 35. The insertion lever is slideable in the opening, and is connected to the gear mechanism 32 inside the casing 30, as will be described. Therefore, when the insertion lever is pushed forward it acts as a pusher means for moving the gear mechanism.

The outer feeding means 33 has a through bore extending axially. The inner feeding means 34 is inserted into the bore of the outer feeding means 33 for axial movement. A similar through bore extends axially through the inner feeding means 34 for accommodating the suture 6 to move axially therein.

Figure 4:
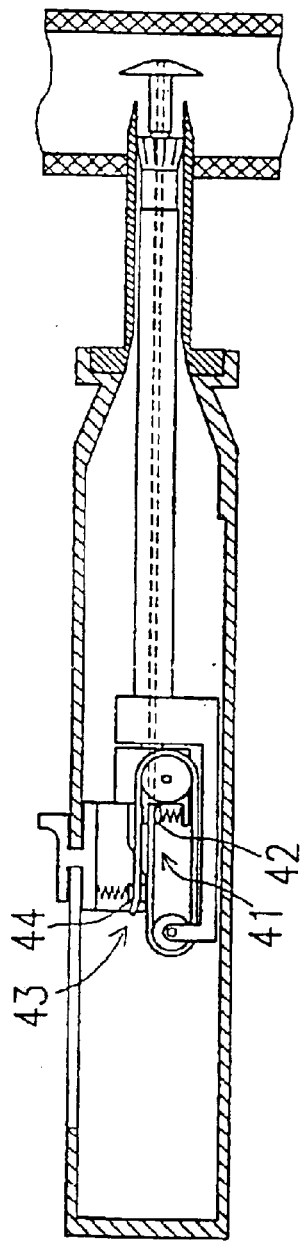
FIG. 4 is a cross sectional view of the embodiment of FIG. 3, when inserting the distal member of a closure plug.
Figure 5:
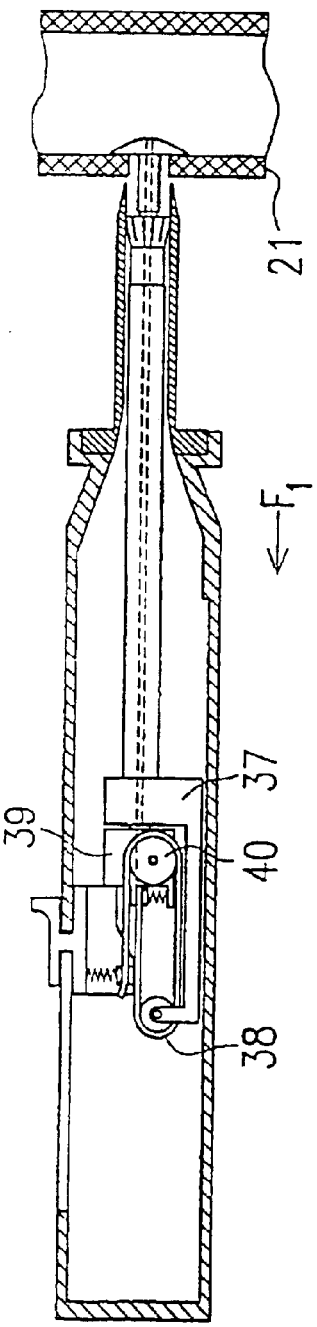
FIG. 5 is a cross sectional view of the embodiment of FIG. 3, when retracting the introducer from the wound.

With reference to FIGS. 4 and 5, the gear mechanism 32 comprises a pulley spacer member 37, for holding the pulley 38 at a distance from the proximal end of the bore through the outer feeding means 34. The pulley spacer member 37 is fixedly attached to the proximal end of the outer feeding means 33, and a bore (not shown) through the pulley spacer member 37 is positioned to form an extension of the bore through the outer feeding means such that the inner feeding means 34 can move freely through the pulley spacer member 37. A first pulley 38 is rotatably attached to the proximal end of the pulley spacer member 37.

The gear mechanism 32 also comprises a clamping block 39, at its distal end fixedly attached to the inner feeding means 34 by means of a bore (not shown) in the clamping block 39 such that the suture can move freely through the clamping block. A second pulley 40 is rotatably attached to the clamping block 39, and is substantially rotating in the same plane as the first pulley 38.

A first brake means 41, consisting of a spring-loaded brake shoe 42, is mounted on the clamping block 39. A second brake means 43, consisting of a spring loaded brake shoe 44, is mounted on the interior part of the insertion lever 36.

The suture 6, having a knot in its distal end so that it does not slip through the bore of the distal plug member 2, runs through the distal plug member 2, through the inner feeding means 34, out from the clamping block 39 were the suture is held in the first brake means 41, around the first pulley 38, back towards the clamping block, around the second pulley 40 to finally be held by the second brake means 43 of the insertion lever 36. The suture is stretched in order to urge the post 7 end surface 14 of the distal plug member 2 against the inner feeding means 34.

The proximal plug member 3 is disposed around the inner feeding means 34 to move along it, but is restricted from moving in the proximal direction by the end of the outer feeding means 33.

The distal end of the casing has a tapered section 45. Therefore, the mouth 46 at the distal end of the tool is more narrow that the outer diameters of the plug members, respectively. However, due to the shape of the plug members and the flexibility of their material they will collapse if pressed through the tapered section 45 out of the mouth 46.

Before use of the tool, the gear mechanism together with all components attached thereto is withdrawn towards the proximal end of the casing 30, as shown in FIG. 3.

An embodiment of a method for closing a wound in a vessel, utilizing the embodiment of an insertion tool as described above, shall now be described.

In a first step of the method of the invention, as shown in FIG. 3, the insertion tool 101 is coupled to an introducer 23 being positioned in the wound in the vessel 20.

In a second step of the method of the invention, as shown in FIG. 4, the insertion tool casing 30 is held essentially stationary with respect to the wound while the insertion lever 36 is pushed towards the wound. The insertion lever 36 abuts against the clamping block 39 to push the clamping block and the pulley spacer member 37 and, consequently, the inner and the outer feeding means 33, 34 towards the wound. Thereby, the plug members 2, 3 are pressed into the tapered section 45 of the casing 30 to collapse to a diameter allowing them to be pushed through the introducer 23.

The length of the opening 35 in which the insertion lever 36 moves, as well as the lengths of other components of the insertions tool 101, are selected to suit the length of the introducer 23 such that when the insertion lever reaches the distal end of the opening to be stopped there, the distal plug member 2 exits out of the introducer 23.

When the distal plug member 2 exits from the introducer 23 it unfolds inside the vessel 20. Thereby, the operator is able to feel a "snap", being a signal that the distal plug member 2 is properly inserted.

Figure 6:
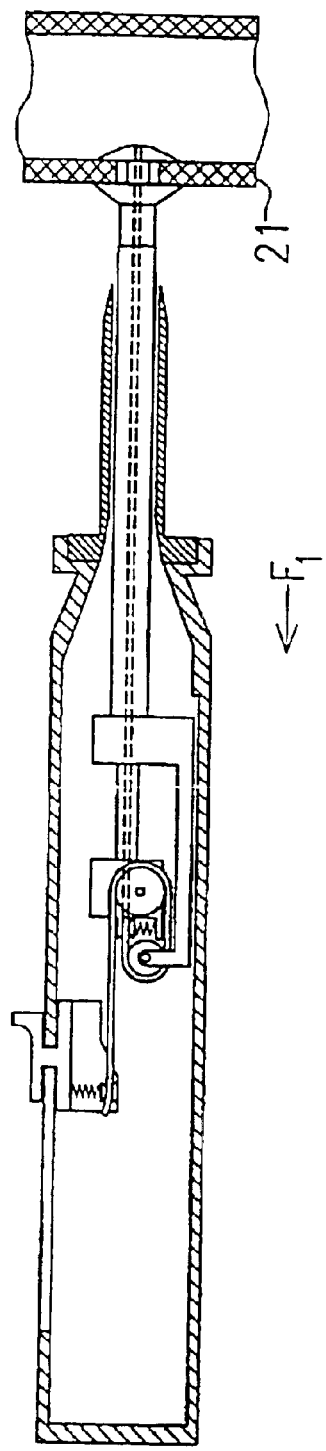
FIG. 6 is a cross sectional view of the embodiment of FIG. 3, when mating the proximal plug member with the distal plug member being disposed inside the vessel.

In a third step of the method of the invention, as shown in FIGS. 5 and 6, the insertion tool 101 together with the introducer 23 is withdrawn from the wound with a force $F_1$ to mate the plug members 2, 3. During this step the distal plug member 2 abuts against the inside of the vessel wall 21 to cover the inside of the edge of the puncture. The force $F_1$ should be controlled by selecting the braking force of the second brake means 43, to be low enough not to rupture the vessel wall around the puncture wound. A typical force for closing a wound in the femoralis artery, which is an artery in which surgical puncture wounds often are opened, without rupturing the vessel is 2 N.

During the withdrawal the suture is stretched (and a tension force is imparted on the suture), around the first pulley 38 and the second pulley 40 and is held at its proximal end by the clamping force of the second brake means 43. The first brake means 41 serves to keep the clamping block 39, and consequently also the inner feeding means 34, at a place with respect to the suture 6. The breaking force of the first brake means is adjusted to be the same as the breaking force of the second brake means.

The distance between the second brake means 43 and the second pulley 40 is constant since the insertion lever 36 abuts the clamping block 39. Therefore, the first pulley 38 is drawn towards the second pulley 40. In this movement, the first pulley 38 pushes the pulley spacer member 37, and consequently the outer feeding means 33 and the proximal plug member 3, towards the distal plug member 2.

The snap fitting of the plug elements is designed to require a snapping force of the same order as the force of withdrawal of the tool, that force being transferred to the proximal plug member as described above. Since the gear ratio of the gear mechanism according to the present invention is approximately unity, the plug members are mated with a force substantially the same as the force with which the tool is drawn away from the patient. The brake means 41, 43 limit this force to prevent it from being higher than the strength of the vessel. Therefore, the saw tooth profile should be designed to allow for mating of the plug members with a force somewhat less than the suture breaking force applied by the brake means.

The mating of plug members 2, 3 continues until the first pulley 38 and the pulley spacer member 37 runs into the second pulley 40 and the clamping block 39, as shown in FIG. 6.

Figure 7:
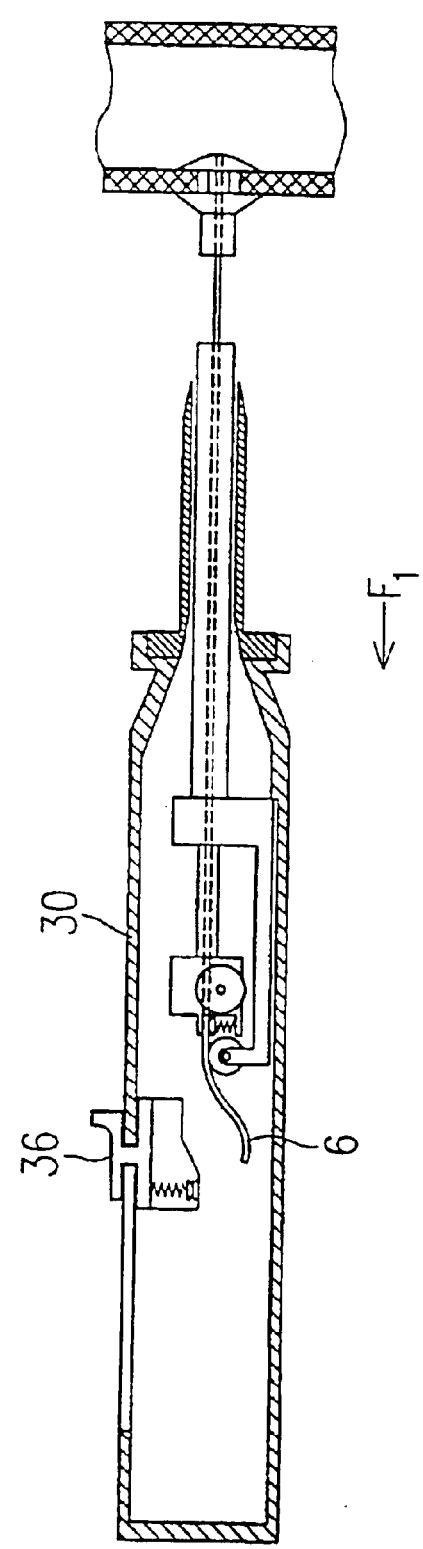
FIG. 7 is a cross sectional view of the embodiment of FIG. 3, when freeing the plug retracting means from the tool.

In a fourth step of the method of the invention, as shown in FIG. 7, the insertion tool 101 together with the introducer 23 is further withdrawn from the patient to finally remove the tool from the wound.

During this continued withdrawal of the tool casing 30 the insertion lever 36 is urged to stretch the distal suture end. The braking force of the second brake means 43 will not be able to hold the suture 6 when the withdrawing force exceeds said braking force, and consequently the suture will become free from the insertion lever. Continued withdrawal of the casing 30 will result in the same effect at the first brake means 41, thereby leaving the suture free from the tool. The suture remains protruding out from the skin end of the wound, and may be cut to a proper length.

It should be noted that the suture acts as a force transmitting means only, and is not used for holding the plug member together after mating or for pressing any of the plug members towards the vessel wall.

A second embodiment of the tool of the invention 102 shall now be described with reference to FIGS. 8-12.

Figure 8:
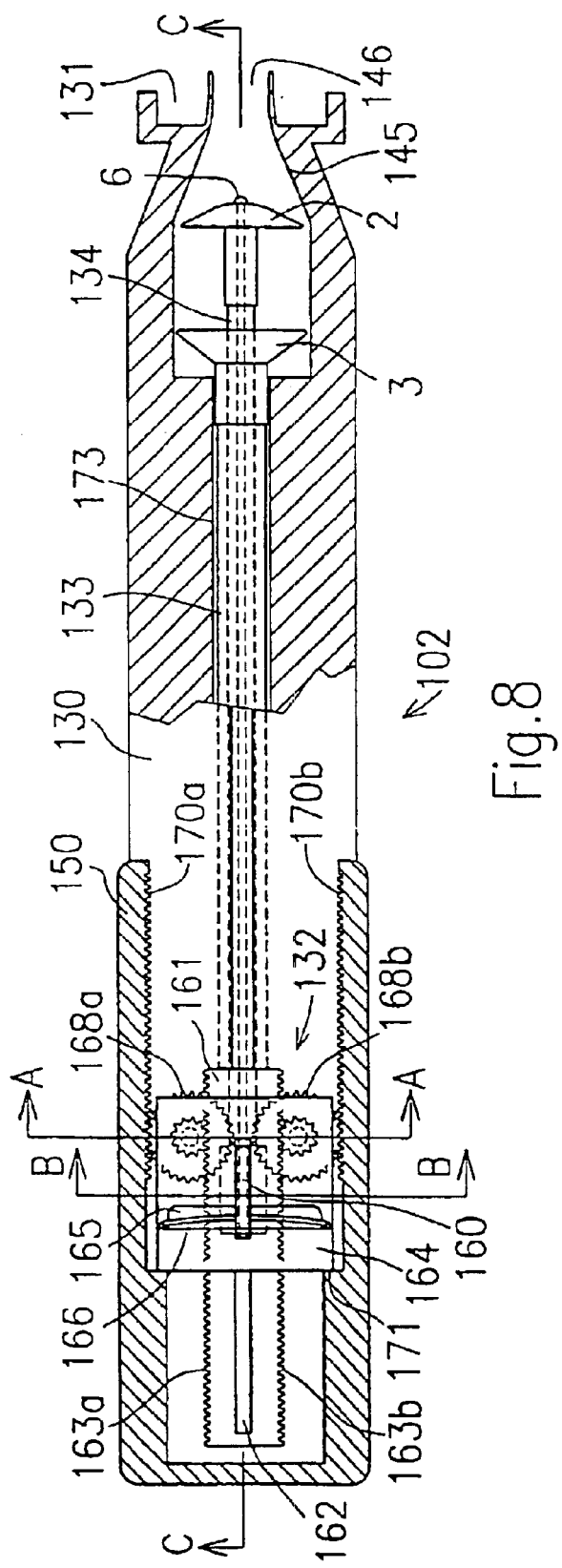
FIG. 8 is a partly cross sectional view of a second embodiment of the tool of the invention.

As seen in FIG. 8, a casing 130, an introducer fitting 131, a tapered end section 145 of the casing 130, and a mouth 146 at the distal end of the tool 102 corresponds to the first embodiment described above. Also, the plug members 2, 3, the suture or retractor 6 and the outer and the inner feeding means or outer feed boom and inner feed boom 133, 134 are initially disposed in the casing 130 as for the first embodiment above. The outer and inner feeding means runs with a clearance through a bore 173 in the casing, said bore 173 being narrow enough to act as a guide that prevents the feeding means from excessive bending in a case where they are formed from a highly flexible material, such as a thermoplastic. Such highly flexible material for forming the feeding means is advantageous in that it improves the flexibility of the feeding means, thereby providing higher freedom of movement within the wound.

The inserting tool 102 comprises a gear mechanism or movement direction reverser 130 of a different design than the gear mechanism or movement direction reverser 32 of the first embodiment. According to the second embodiment, the proximal end of the inner feeding means or inner feed boom 134 is formed as a block section 160 protruding towards the viewer of FIG. 8, while the proximal end of the outer feeding means or inner feed boom 133 is formed as a plate section 161 extending axially with respect to the outer feeding means and perpendicularly with respect to the block section 160. The block section 160 extends through an axial opening 162 in the plate section 161 to be axially movable in the opening 162.

The longitudinal sides of the plate section 161 of the outer feeding means 133 are provided with cog profiles 163a, 163b.

An upper plate 164 in which a substantially T-shaped opening 165 is formed is positioned above, and substantially parallel with, the plate section 161 such that the block section 160 extents through the "leg" of the T-opening. A wire spring 166 is biased into the T-opening, transverse to the "leg", and runs through a small hole in the block section 160 to press the upper plate 164 towards the block section 160.

Figure 9:
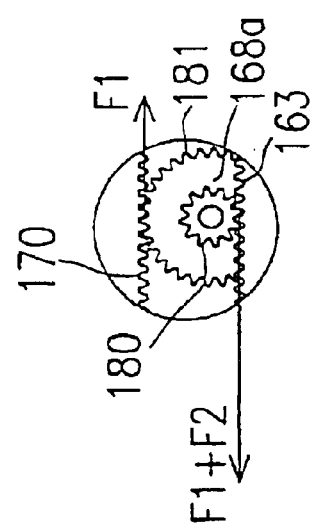
FIG. 9 is a detailed view of forces acting on a double gear wheel used in the second embodiment of the tool according to the invention.

Two double gear wheels 168a, 168b, each one having a small gear ring 180 and a large gear ring 181 (as seen in FIG. 9) being fixed with respect to each other, are rotatably mounted in the upper plate 164. The gear wheels 168a, 168b are disposed one at each side of the plate section 161 such that the small gear ring 180 of each gear wheel engages the cog profile 163a, 163b of the respective side of the plate section 161.

Figure 10:
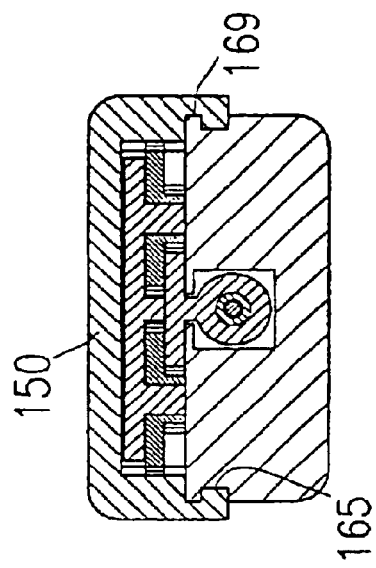
FIG. 10 is a cross sectional view of the tool according to FIG. 8, seen along the line AA in FIG. 8.

A cover or retractor 150 being axially slideable in guides 169 in the casing 130 covers the plate section 161, the upper plate 164 and their associated components, as shown in FIGS. 8, 10 and 11. Two inner gear racks 170a, 170b, one at each inner side of the cover 150, runs axially inside the cover. When the cover is mounted on the casing, the large gear rings of the double gear wheels 168a, 168b are engaged with the gear racks 170a, 170b, respectively.

The upper plate 164 abuts against an inner seat 171 of the cover 150. When the cover 150 is pushed forward with respect to the casing 130, i.e. in a distal direction, it pushes the upper plate 164 forward as well, and brings with it the other components of the gear mechanism. Therefore, when the cover is pushed forward it acts as a pusher means for moving the gear mechanism.

As shown in FIG. 12, the proximal end of the suture 6 ends in a small recess in the substantially T-shaped opening 165 of the upper plate 164, and is stretched and clamped between the block section 160 of the inner feeding means 134 and the upper plate 164 by means of the wire spring 166. The bias of the % wire spring is selected, to apply a suture holding force lower than the rupture pull force of the vessel. The suture holding force corresponds to the force with which the tool is drawn away from the wound during use.

It should be noted that it is possible to design a gear mechanism having one double gear wheel, cog profile and gear rack set only, if the other set it replaced by a guide means to allow for a proper linear movement. However, the embodiment being described herein with reference to FIGS. 8-17 is presently assessed to provide a more reliably performance.

A second embodiment of the method for closing a wound in a vessel, utilizing the second embodiment of the insertion tool 102, shall now be described with reference in to FIGS. 13-17.

In the first step of the second embodiment of the method of the invention, as shown in FIG. 13, the insertion tool 102 is coupled to an introducer 123 being positioned in the wound and extending through the wall of the vessel.

In the second step of the second embodiment of the method of the invention, as shown in FIG. 14, the insertion tool casing 130 is held essentially stationary with respect to the wound while the cover 150 is pushed towards the wound. As described above, when pushed forward, the cover 150 brings the upper plate 164 forward as well. As both the inner and the outer feeding means 133, 134 are coupled to the upper plate they are pushed through the introducer 123 towards the wound. Thereby, the plug members 2, 3 are pressed into the tapered section 145 of the casing 130 to collapse to a diameter allowing them to be pushed through the introducer 123.

The cover 150 is pushed forward (i.e. in the distal direction) until the distal plug member 2 exits from the introducer 123 to unfold itself inside the vessel 20. When the distal plug member 2 unfolds this is registered by the operator as a "snap".

As for the first embodiment, the dimensions of the parts involved are selected to suit the length of the introducer 123.

Figure 16:
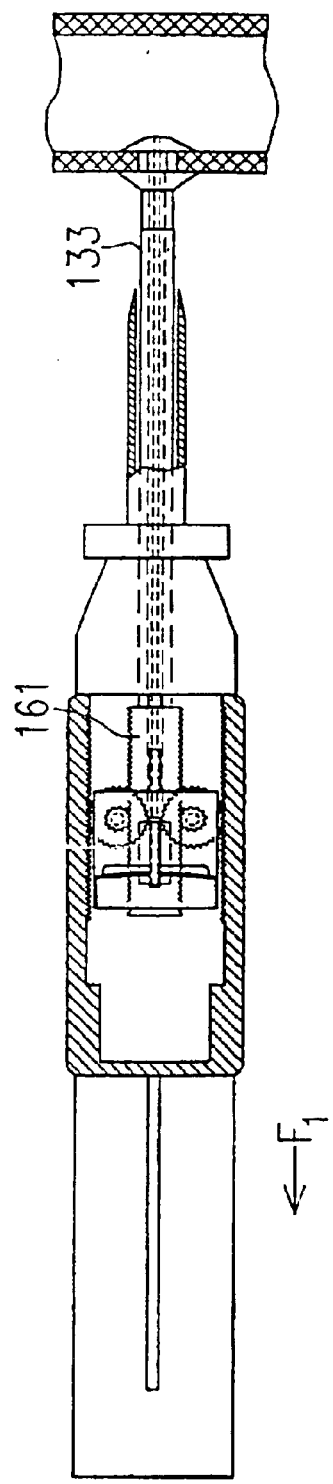
FIG. 16 is a cross sectional view of the embodiment of FIG. 13, when mating the proximal plug member with the distal plug member being disposed inside the vessel.

In the third step of the second embodiment of the method of the invention, as shown in FIGS. 15 and 16, the insertion tool 102 together with the introducer 123 is withdrawn from the wound with a force F1 to mate the plug members 2, 3 corresponding to what has been previously described for the first embodiment.

However, the gear mechanism 132 of the second embodiment provides a gear ratio higher than unity, thereby enabling the plug members 2, 3 to be mated with a force higher than the withdrawing force of the tool. This shall now be described.

As the operator pulls the insertion tool 102 an ay from the wound subsequent to the unfolding of the distal plug member, the cover 150 abuts against a stopping means, such as a step-shaped edge 172 (see FIG. 12) ex tending from the casing 130. Therefore, as the casing 130 is pulled further away from the patient, the cover 150 follows this movement while the suture 6 remains stretched to keep the block section 160 at a substantially constant distance from the distal plug member.

At the same time, the stretching force in the suture is transferred to the upper plate 164 via the block section 160. However, as the cover 150 and consequently the gear racks 170a, 170b are pushed with the force F1 with respect to the suture, this force F1 acts on the large gear ring 181 of each gear wheel 168a, 168b, respectively, to rotate the gear wheels. Due to lever action, this creates a force F1+F2 in the small gear rings 180 to act on the cog profiles 163a, 163b of the plate section 161 (see FIG. 9) for driving the plate section in the opposite direction with respect to the tool pulling force, i.e. in the distal direction.

Thus, although the casing 130 and the cover 150 are pulled away from the distal plug member 2 with a force $F_1$, the plate section 161 strives towards the distal plug member 2 with the force $F_1+F_2$. As the plate section 161 moves in the distal direction, the outer feeding means 133 moves with it towards the distal plug member 2.

Therefore, the proximal plug means 3 is mated with the distal plug means 2 with the force $F_1+F_2$.

Figure 17:
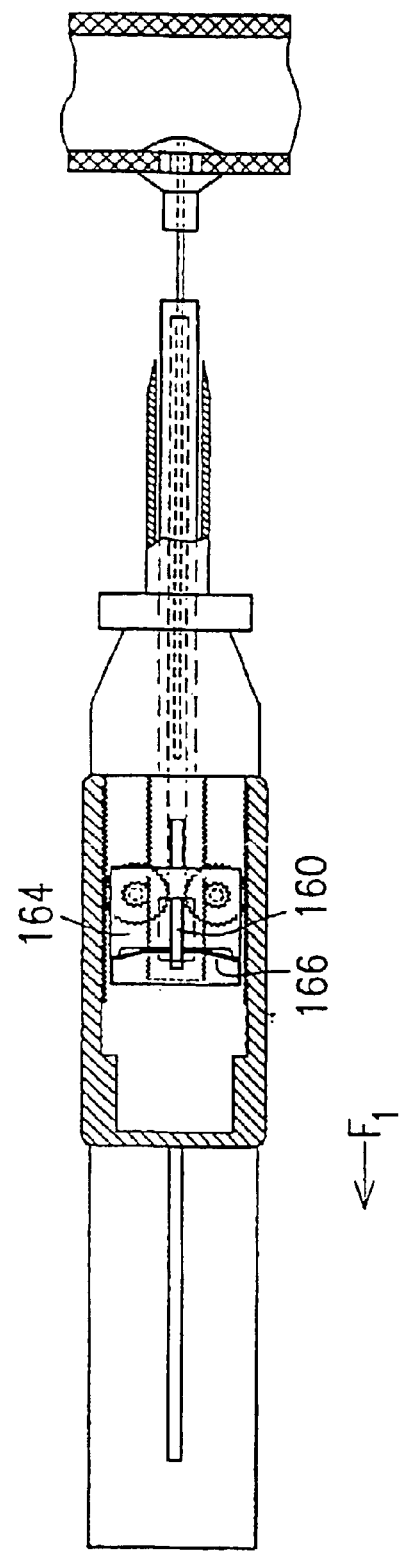
FIG. 17 is a cross sectional view of the embodiment of FIG. 13, when freeing the plug retracting means from the tool.

In the fourth step of the second embodiment of the method of the invention, as shown in FIG. 17, the tool 102 is further withdrawn from the patient to finally remove the tool from the wound.

During this continued withdrawal of the tool, the withdrawing force now acts on the point where the proximal end of the suture 6 is clamped between the upper plate 164 and the block section 160. When the pulling force exceeds the force of the wire spring 166 acting of the suture via the block section, the spring will loose its grip on the suture and the suture will slip out of the inner bore of the inner feeding means of the tool. The suture may then be cut to a proper length.

Using the method and the tool according to the second embodiment of the invention is preferred as compared to the first embodiment since the additional mating force $F_2$ allows the edges of the wound to be positively clamped between the plug members to ensure a safe closure of the wound even in a case where the material of the plug relaxes somewhat after insertion.

Using the tool of the present invention has many advantages.

No ordinary skill is required to ensure that the intraarterial member of the closure plug is entirely inserted into the vessel, since this is taken care of by designing of the tool with suitable dimensions with respect to the introducer.

The "snap" feeling gives a positive indication to the operator that the intra-arterial member of the closure plug has unfolded properly.

The entire closing procedure is performed by the simple and natural withdrawing movement of the tool from the wound. The operator only has to take care not to withdraw the tool too fast from the wound, thereby exceeding the mechanical response in the gear mechanism.

There is no need for the operator to monitor a force gauge, since the brake means applied to the retracting means are preset to loosen their grip on the retracting means if an excessive withdrawing force is applied. Therefore, the risk of rupturing the vessel is considerably reduced.

What is claimed is:

1. A tool (101; 102) for inserting and mating two bioabsorbable plug members (2, 3) of a sealing device (1) for closing a wound in the wall of a blood vessel, one bioabsorbable plug member of the sealing device being a bioabsorbable distal plug member (2) to be positioned inside the blood vessel and the other bioabsorbable plug member being a bioabsorbable proximal plug member (3) to be positioned outside of the blood vessel, the bioabsorbable distal plug member being provided with an elongated retracting means (6) extending from the bioabsorbable distal plug member, wherein the tool comprises a gear mechanism (32; 132) coupled to the retracting means for converting a movement of the tool in a proximal direction away from the wound, when the bioabsorbable distal plug member is anchored in the blood vessel, to a pushing movement for moving the bioabsorbable proximal plug member in a direction towards the bioabsorbable distal plug member, the pushing movement being induced by a stretching force ($F_1$) in the retracting means.

2. The tool (101; 102) according to claim 1, wherein the tool comprises a spring-biased coupling means (41; 164, 166) for releasably coupling the retracting means (6) to said gear mechanism (32; 132).

3. The tool (101; 102) according to claim 2, wherein the biasing force of said spring-biased coupling means (41; 164, 166) is selected to release the retracting means (6) when the stretching force ($F_1$) in the retracting means exceeds a selected force attributed to the rupture-tension of the wall of the blood vessel.

4. The tool (101; 102) according to claim 1, wherein said tool comprises:

an outer feeding means (33; 133) for pushing the bioabsorbable proximal plug member (3), said outer feeding means being provided with an axial through bore;

an inner feeding means (34; 134) for pushing the bioabsorbable distal plug member (2), said inner feeding means being provided with an axial through bore for moveably receiving said retracting means (6), said inner feeding means being disposed for movement in said bore of said outer feeding means, said gear mechanism (32; 132) being coupled to said inner feeding means and said outer feeding means; and a pushing means (36; 150) for pushing the gear mechanism (32; 132), the outer feeding means (33; 133), and the bioabsorbable proximal plug member (3), with respect to a casing (30; 130) of the tool, in a direction towards the wound.

5. The tool (102) according to claim 4 wherein said gear mechanism (132) comprises at least one of a set, the set comprising:

a gear rack (170a, 170b) fixed to said pushing means (150);

a cog rail (163a, 163b) connected to said outer feeding means (133);

a double gear wheel (168a, 168b) having a small gear ring (180) and a large gear ring (181) fixed with respect to each other, said double gear wheel being rotatably connected to a plate member (164), said large gear ring (181) being in engagement with said gear rack (170a, 170b), and said small gear ring (180) being in engagement with said cog rail (163a, 163b); wherein said plate member (164) is arranged to move with said outer feeding means and said plate member releasably holds the retracting means by means of a spring (166), the retracting means being moveably disposed in the bore of said inner feeding means, and wherein said set is thereby cooperatively arranged to convert a proximal movement of said tool to a distal movement of said outer feeding means when the retracting means is stretched.

6. The tool (101) according to claim 4 wherein said gear mechanism (32) comprises:

a first pulley (38) attached to said outer feeding means via a spacer member (37);

a second pulley (40) attached to said inner feeding means (34);

a first brake means (41) attached to said inner feeding means;

a second brake means (43) attached to said pushing means (36); wherein the retracting means (6) is arranged such that it extends from the bioabsorbable distal plug member (2) in a proximal direction, through said bore of said inner feeding means (33), through the first brake means (41), around said first pulley (38) to be redirected to a distal direction, around said second pulley (38) to be redirected again to the proximal direction, and through said second brake means (43).

7. A method for closing a wound in a punctured blood vessel with a tool, comprising:

inserting and mating two plug members (2, 3) of a sealing device (1), one plug member of the sealing device being a distal plug member (2) to be positioned inside the blood vessel and the other plug member being a proximal plug member (3) to be positioned outside of the blood vessel, the distal plug member being provided with an elongated retracting means (6) extending from the distal plug member;

positioning the distal plug member (2) inside the blood vessel with the retracting means (6) being attachable to the tool comprising a gear mechanism (32; 132) connectable to the retracting means for converting a movement of the tool in a proximal direction away from the wound, to a pushing movement for moving the proximal plug member in a direction towards the distal plug member in response to a stretching force ($F_1$) in the retracting means when the distal plug member is anchored in the blood vessel; and withdrawing the tool (101; 102) with the retracting means attached thereto to stretch the retracting means, thereby activating the gear mechanism to approach the proximal plug member towards the distal plug member via a feeding means (34;134).

8. The method according to claim 7, wherein said tool (101; 102) comprises a spring-biased coupling means (41; 164, 166) for releasably coupling the retracting means (6) to said gear mechanism (32; 132).

9. A system for closing a wound in a punctured blood vessel, comprising:

obtaining a sealing device comprising:

a distal resiliently expandable plug member (2) having an elongated retracting means extending centrally from a distal plug member and including a portion (10) for attaching a proximal plug member (3) of the sealing device, the proximal plug member being resiliently expandable and being adapted to be mounted onto the distal plug member to be fixed thereto by means of the attaching portion, wherein the proximal plug member comprises a through bore (9), the distal plug member comprises a through bore (8), and a suture (6) is passed through said bore (8) to serve as the retracting means by providing an enlarged portion at one end as a counter when pulling the suture; and inserting and mating the sealing device using a tool, the tool comprising:

a gear mechanism coupled to the retracting means for converting a movement of the tool in a proximal direction away from the wound, when the distal plug member is anchored in a blood vessel, to a pushing movement for moving the proximal plug member in a direction toward the distal plug member, the pushing movement being induced by a stretching force in the retracting means.

10. A tool (101; 102) for closing a wound by positioning a bioabsorbable distal plug inside a blood vessel and a bioabsorbable proximal plug positioned outside of the blood vessel, comprising:

a casing; and a movement direction reverser (32; 132) adapted to be coupled to a retractor which is coupled to the bioabsorbable distal plug, wherein the movement direction reverser, when coupled to the retractor, is adapted to convert movement of the casing in a proximal direction away from the wound when the bioabsorbable distal plug is anchored in the blood vessel to a pushing movement to move the bioabsorbable proximal plug in a direction towards the bioabsorbable distal plug, the pushing movement to move the bioabsorbable proximal plug being induced by a tension force imparted on the retractor.

11. The tool (101; 102) according to claim 10, wherein the tool comprises a spring-biased coupling (41; 164, 166) adapted to releasably couple the retractor (6) to the movement direction reverser (32; 132).

12. The tool (101; 102) according to claim 11, wherein the biasing force of said spring-biased coupling (41; 164, 166)

is sufficient to release the retractor (6) when the force imparted on the retractor exceeds a selected force based on the rupture-tension of a wall of the blood vessel.

13. The tool (101; 102) according to claim 10, wherein said tool comprises:
   an outer feed boom (33; 133) adapted to push the bioabsorbable proximal plug (3), said outer feed boom being provided with an axial through bore;
   an inner feed boom (34; 134) adapted to push the bioabsorbable distal plug (2), said inner feed boom being provided with an axial through bore adapted to moveably receive said retractor (6), said inner feed boom being further adapted to move in said bore of said outer feed boom, said movement direction reverser (32; 132) being coupled to said inner feed boom and said outer feed boom; and
   a pusher (36; 150) adapted to push the movement direction reverser (32; 132), the outer feed boom (33; 133), and the bioabsorbable proximal plug (3), with respect to the casing (30; 130) of the tool, in a direction towards the wound.

14. The tool (102) according to claim 13 wherein said movement direction reverser (132) comprises at least one of a set of components, the set of components comprising:
   a gear rack (170a, 170b) fixedly connected to said pusher (150);
   a cog rail (163a, 163b) fixedly connected to said outer feed boom (133);
   a double gear wheel (168a, 168b) having a small gear ring (180) and a large gear ring (181) fixed with respect to each other, said double gear wheel being rotatably connected to a plate (164), said large gear ring (181) being in engagement with said gear rack (170a, 170b), and said small gear ring (180) being in engagement with said cog rail (163a, 163b); wherein
   said plate (164) is arranged to move with said outer feed boom, and said plate is adapted to releasably hold the retractor with a device including a spring (166), the retractor being moveably disposed in the bore of said inner feed boom, and wherein
   said set is cooperatively arranged and adapted to convert a proximal movement of said casing to a distal movement of said outer feed boom in conjunction with a tension force on the retractor.

15. The tool (101) according to claim 13 wherein said movement direction reverser (32) comprises:
   a first pulley (38) attached to said outer feed boom via a spacer (37);
   a second pulley (40) attached to said inner feed boom (34);
   a first brake (41) attached to said inner feed boom;
   a second brake (43) attached to said pusher (36); wherein
   the retractor (6) is arranged such that when the retractor is coupled to the movement direction reverser, the retractor extends from the bioabsorbable distal plug (2) in a proximal direction, through said bore of said inner feed boom (33), through the first brake (41), around said first pulley (38) to be redirected in a distal direction, around said second pulley (38) to be redirected to the proximal direction, and through said second brake (43).

16. The tool (101; 102) according to claim 10, further comprising the retractor.

17. A method for closing a wound in a punctured blood vessel utilizing two plugs (2, 3) of a sealing device (1), comprising:
   inserting a distal plug (2) through a wound and positioning the distal plug inside the blood vessel and positioning a proximal plug (3) outside the blood vessel, the distal plug being provided with a retractor (6) extending from the distal plug;
   pushing the proximal plug towards the distal plug with a tool comprising a casing and a movement direction reverser (32; 132) coupled to the retractor by converting a movement of the casing in a proximal direction away from the wound to a pushing movement to move the proximal plug in a direction towards the distal plug, the pushing movement to move the proximal plug being induced by a tension force on the retractor.

18. The method of claim 17, wherein movement of the casing in the proximal direction results from withdrawing the tool (101; 102) with the retractor attached to the tool, wherein the tension force on the retractor results from withdrawing the tool (101; 102) with the retractor attached to the tool and the distal plug (2) anchored in the blood vessel, and wherein the tension force on the retractor induces the movement direction reverser to drive the proximal plug towards the distal plug.

19. The method according to claim 17, wherein said tool (101; 102) comprises a spring-biased coupling (41; 164, 166) adapted to releasably couple the retractor (6) to said movement direction reverser (32; 132).

20. A sealing device (1) comprising:
   a distal resiliently expandable plug (2) having an elongated retractor extending centrally from the distal resiliently expandable plug and including an attaching portion (10) adapted to attach to a proximal plug (3) of the sealing device, the proximal plug being resiliently expandable and being adapted to be mounted onto the distal plug and to be fixed thereto by the attaching portion, wherein
   the distal plug comprises a through bore (8), and a suture (6), the suture extending through said bore (8) and forming at least a portion of the retractor, the suture having an enlarged portion at one end that is adapted to provide a counter surface when a tension force is imparted on the suture, wherein
   the sealing device is inserted and mated by the use of a tool, wherein the tool comprises a movement direction reverser coupled to the retractor and adapted to convert movement of at least a portion of the tool in a proximal direction away from the wound, when the distal plug is anchored in a blood vessel, to a pushing movement for moving the proximal plug in a direction toward the distal plug, the pushing movement to move the proximal plug being induced by a tension force in the retractor.

21. The sealing device according to claim 20, wherein the distal plug is bioabsorbable.

22. The sealing device according to claim 20, wherein the proximal plug is bioabsorbable.

* * * * *